US012551378B2

(12) United States Patent
Weidert

(10) Patent No.: US 12,551,378 B2
(45) Date of Patent: Feb. 17, 2026

(54) VENTILATION UNIT AND CONTROLLER DEVICE

(71) Applicant: Otex Protective Inc., Rochester, NY (US)

(72) Inventor: Jacob R. Weidert, Rochester, NY (US)

(73) Assignee: Otex Protective Inc., Rochester, NY (US)

(*) Notice: Subject to any disclaimer, the term of this patent is extended or adjusted under 35 U.S.C. 154(b) by 1174 days.

(21) Appl. No.: 17/367,332

(22) Filed: Jul. 3, 2021

(65) Prior Publication Data

US 2021/0330506 A1 Oct. 28, 2021

Related U.S. Application Data

(63) Continuation-in-part of application No. 15/730,519, filed on Oct. 11, 2017, now Pat. No. 11,051,984.

(60) Provisional application No. 62/407,802, filed on Oct. 13, 2016.

(51) Int. Cl.
*A61F 9/06* (2006.01)
*B23K 9/32* (2006.01)
*F16P 1/06* (2006.01)

(52) U.S. Cl.
CPC .............. *A61F 9/068* (2013.01); *B23K 9/322* (2013.01); *F16P 1/06* (2013.01)

(58) Field of Classification Search
CPC . A61F 9/068; A61F 9/06; A61F 9/065; B23K 9/322; F16P 1/06; A62B 9/006; A62B 17/00; A62B 17/04; A62B 18/06; A62B 18/045; A62B 18/08
See application file for complete search history.

(56) References Cited

U.S. PATENT DOCUMENTS

| | | | |
|---|---|---|---|
| 8,223,466 | B2 | 7/2012 | Roscoe |
| 2001/0032348 | A1 | 10/2001 | Diaz |
| 2012/0051904 | A1 | 3/2012 | Hagen et al. |
| 2014/0166001 | A1 | 6/2014 | Kooken |
| 2015/0320601 | A1 | 11/2015 | Gregg |

(Continued)

OTHER PUBLICATIONS

Cal, J. et al. "Demonstration of an optoelectronic 4-bit analog-to-digital converter using a thyristor smart comparator", Oct. 1, 2000, Optics Communication, 184, pp. 79-88. (Year: 2000).

(Continued)

*Primary Examiner* — Margaret M Luarca
(74) *Attorney, Agent, or Firm* — Harris Beach Murtha Cullina PLLC; Neal L. Slifkin

(57) ABSTRACT

A ventilation unit and controller device comprises a ventilation unit with a housing. The housing has an intake port permitting flow of gas into the housing and an exhaust port permitting flow of gas out of the housing. Within the housing, a motorized fan is positioned to direct gas into the housing via the intake port and out of the housing via the exhaust port. A controller capable of controlling the ventilation unit communicates with a sensor capable of detecting an environmental stimulus and responding thereto. A source of electric current provides power to the ventilation unit and controller device. The device is capable of being removably attached via fasteners to an arc flash hood, and the arc flash hood comprises a ventilation opening to permit gas discharged by the device to enter the arc flash hood.

4 Claims, 12 Drawing Sheets

(56) References Cited

U.S. PATENT DOCUMENTS

| | | | | |
|---|---|---|---|---|
| 2016/0276821 | A1 | 9/2016 | Politis | |
| 2016/0297025 | A1 | 10/2016 | Enyedy | |
| 2017/0259089 | A1 | 9/2017 | De Jesus | |
| 2018/0036562 | A1 * | 2/2018 | Patel ...................... | A62B 9/006 |

OTHER PUBLICATIONS

Moaiyeri, Mohammad et al., "An Efficient Analog-to-Digital Converter Based on Carbon Nanotube FETs", 2016, Journal of Low Power Electronics, 12, pp. 150-157. (Year: 2016).

* cited by examiner

VENTILATION UNIT AND CONTROLLER DEVICE

CROSS-REFERENCE TO RELATED APPLICATIONS

The present invention claims priority from pending U.S. Provisional patent application, Ser. No. 62/407,802, filed Oct. 13, 2016, titled "Ventilation Controller for Arc Flash Hood," and U.S. patent application Ser. No. 15/730,519, filed Oct. 11, 2017, the disclosures of which are incorporated herein by reference in their entirety.

TECHNICAL FIELD

The present invention relates to the field of personal protective equipment; more particularly, to a ventilation controller for use with an arc flash hood or protective suit that is capable of stopping or slowing the input of outside air following an arc flash or other hazardous events.

BACKGROUND OF THE INVENTION

Personal protective equipment, or PPE, includes special clothing that protects the wearer from hazardous conditions encountered during electrical work, such as when a large amount of electricity jumps, or arcs, from a charged conductor to ground. Such an arc contains a great amount of energy and can generate a great amount of light and heat. In some conditions, an arc flash can vaporize electrical conductors, including conductors made of materials such as copper or manganese. Harmful chemicals caused by arc flash events include vaporized copper fumes and vaporized manganese fumes. A person of ordinary skill in the art would know of other hazardous chemicals present following an arc flash event.

Arc flash PPE can include clothing that covers the body. A person of ordinary skill in the art would be familiar with an arc flash suit. Arc flash PPE can also include a hood that is worn over the head. Such hoods can include portions that hang down beyond the head to cover the neck and possibly overlap to some extent with the torso portion of an arc flash suit. An arc flash hood has a viewing port, typically including some transparent material, so that the wearer can see outside the hood. A person of ordinary skill in the art would be familiar with an arc flash hood.

Because an arc flash hood covers the head and face, it can restrict the amount of fresh, breathable air available to a user wearing the arc flash hood. Arc flash hoods or arc flash suits can be equipped with ventilation units that input ambient air and provide that air into the interior region that includes the user's breathing space.

In accordance with one aspect of the invention, the invention is intended to prevent or reduce the input of harmful gases or other chemicals into the breathable air inside an arc flash hood or suit. According to the present invention, a sensor detects an arc flash and a controller stops or reduces the input of outside air into the space within the arc flash hood or suit that contains breathable air. This can be accomplished by stopping or slowing a ventilation fan. It can also be accomplished by slowing the speed of a ventilation fan. It can also be accomplished by closing a valve or diverter or other mechanical device capable of restricting the input of ambient air.

According to one aspect of the invention disclosed and claimed herein, the invention comprises a controller for a ventilation unit. According to another aspect of the invention disclosed and claimed herein, the invention comprises a ventilation unit capable of operation in conjunction with a controller that detects and responds to an arc flash or other dangerous conditions. According to another aspect of the invention disclosed and claimed herein, the invention comprises a ventilation unit that includes a controller that detects and responds to arc flash or other dangerous conditions. According to another aspect of the invention disclosed and claimed herein, the invention comprises an arc flash hood that includes a ventilation unit that includes a controller that detects and responds to an arc flash or other dangerous conditions. According to another aspect of the invention disclosed and claimed herein, the invention comprises an arc flash protective suit that includes a ventilation unit that detects and responds to an arc flash or other dangerous condition. According to another aspect of the invention disclosed and claimed herein, the invention comprises a ventilation unit capable of operation in conjunction with a controller that responds to signals detected by a sensor or sensors to control ventilation in the arc flash hood.

The intention of the invention is to stop or slow the fan inside the ventilation unit once an electric arc flash is detected. The purpose is to reduce the introduction of air, which may be compromised, into a protective hood.

The invention will use either one, or multiple sensors, in a series, or not in a series, to detect when an arc flash has occurred. The sensor(s), when triggered, will sever the circuit and cut power to the fan.

SUMMARY

In accordance with one embodiment of the present invention, a ventilation unit and controller device comprises a ventilation unit with a housing, where the housing has an intake port permitting flow of gas into the housing and an exhaust port permitting flow of gas out of the housing. Within the housing, a variable speed motorized fan is positioned to direct gas into the housing via the intake port and out of the housing via the exhaust port. A controller capable of controlling the ventilation unit communicates with a sensor capable of detecting an environmental stimulus. A source of electric current provides power to the ventilation unit and controller device. In addition, the device may comprise a switch capable of interrupting the electric current that powers the device.

BRIEF DESCRIPTION OF THE DRAWINGS

The present invention will now be described, by way of example, with reference to the accompanying drawings, in which.

DETAILED DESCRIPTION

Figure 1:
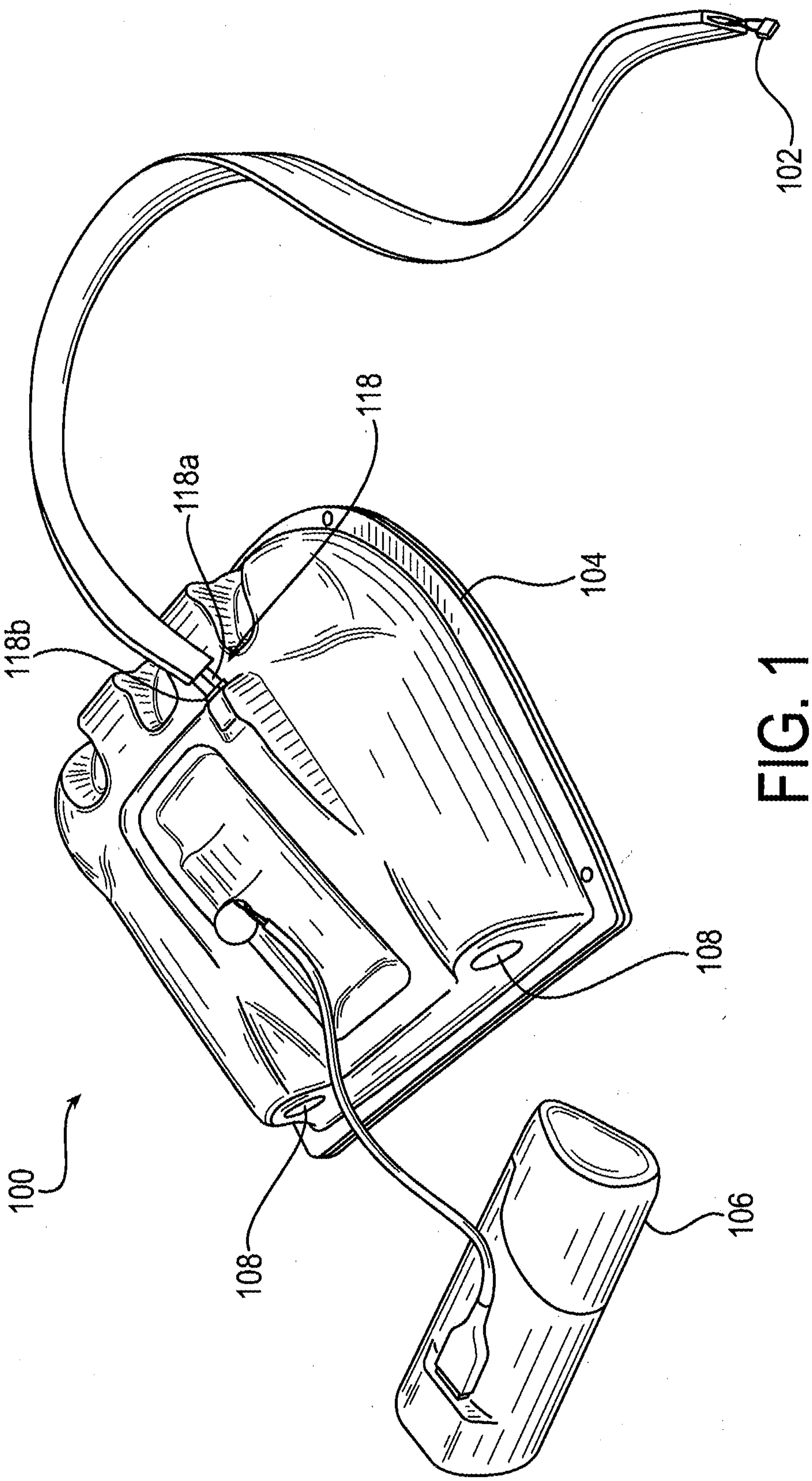
FIG. 1 is a rear perspective view of a ventilation unit and controller device.
Figure 2:
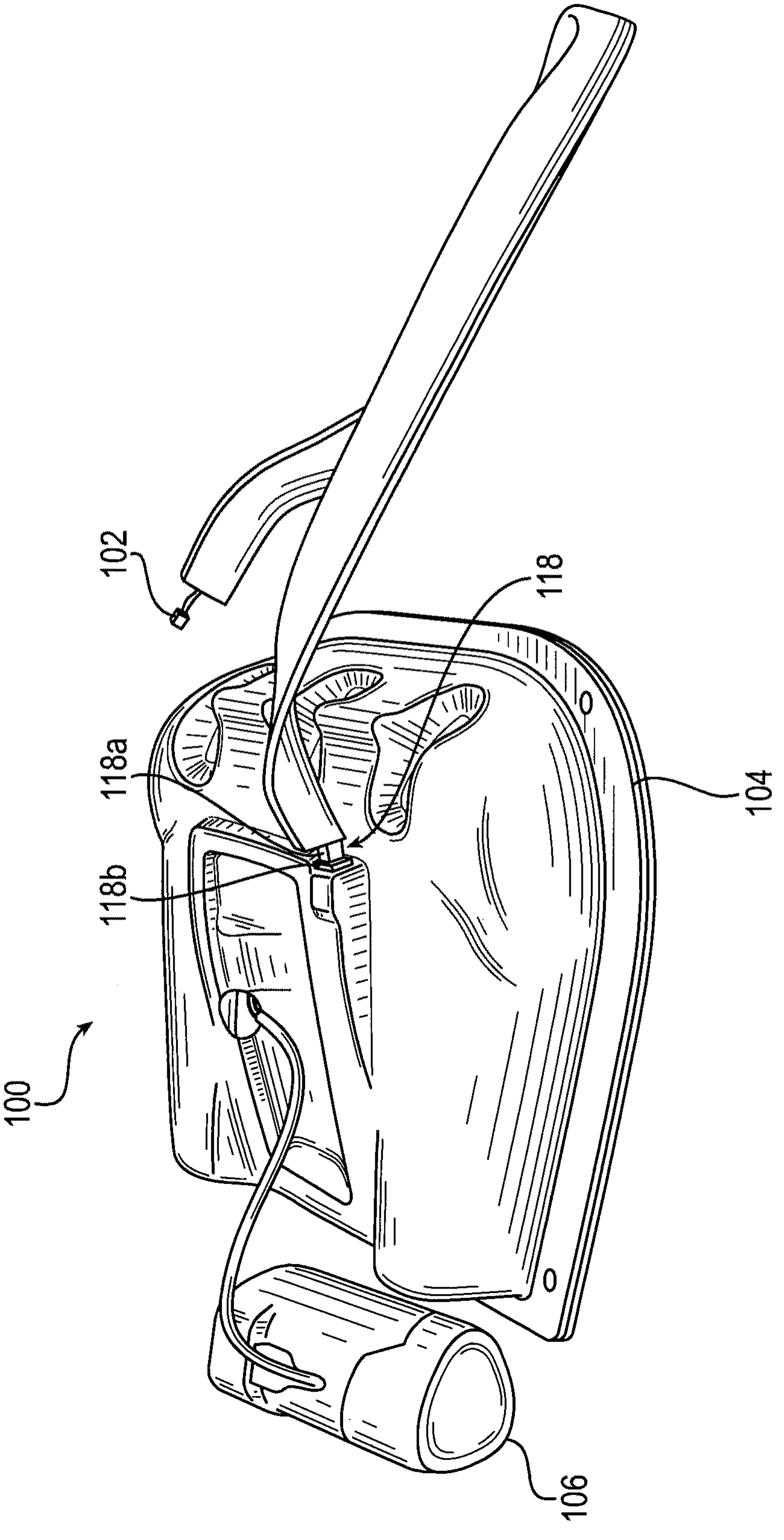
FIG. 2 is an elevated side view of a ventilation unit and controller device.
Figure 3:
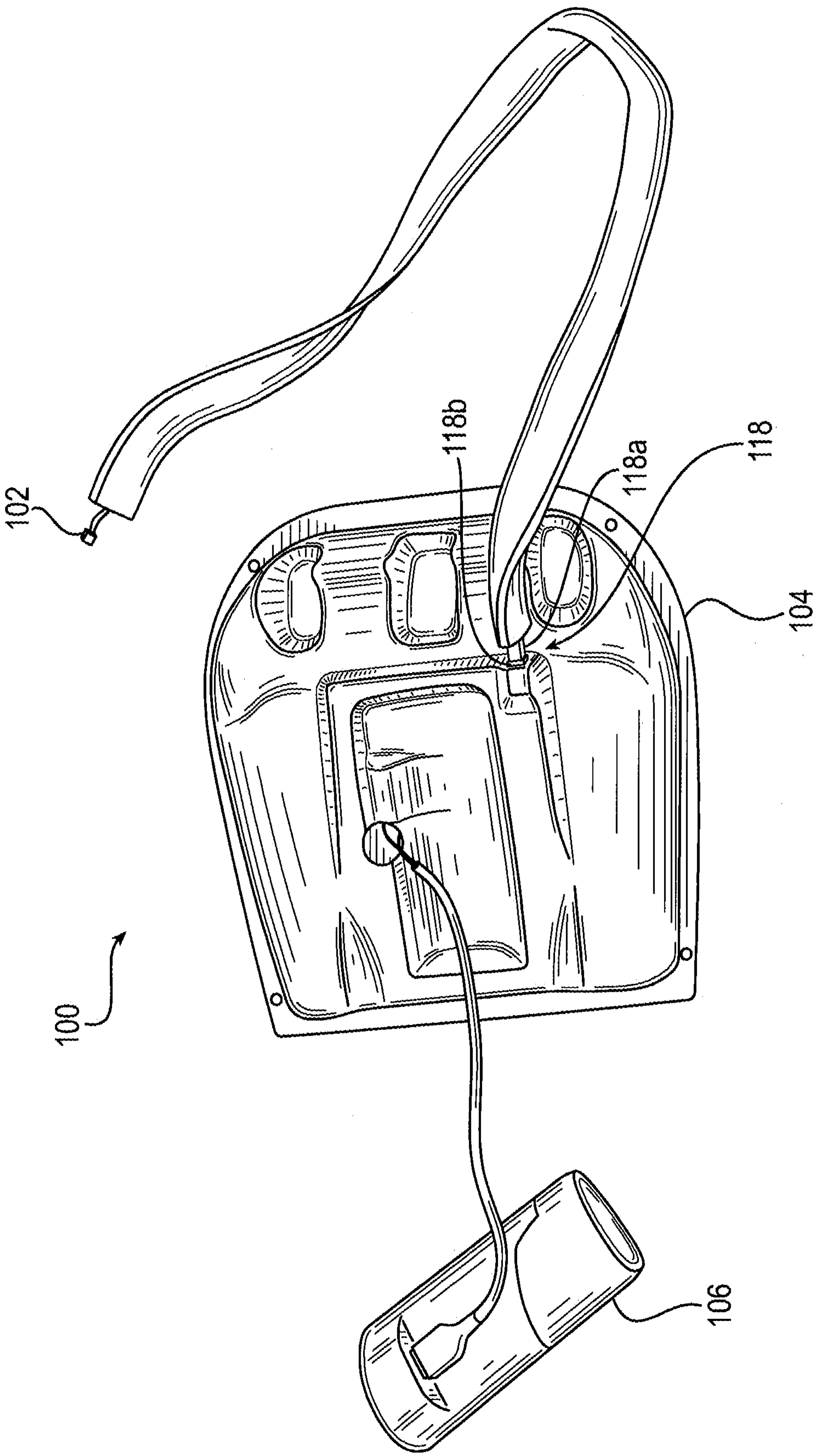
FIG. 3 is a top plan view of a ventilation unit and controller device

Throughout the following description, specific details are set forth in order to provide a more thorough understanding of the invention. However, the invention may be practiced without these particulars. In other instances, well known elements have not been shown or described in detail to avoid unnecessarily obscuring the disclosure. Accordingly, the specification and drawings are to be regarded as illustrative rather than restrictive. It is to be further noted that the drawing are not to scale.

Figure 4:
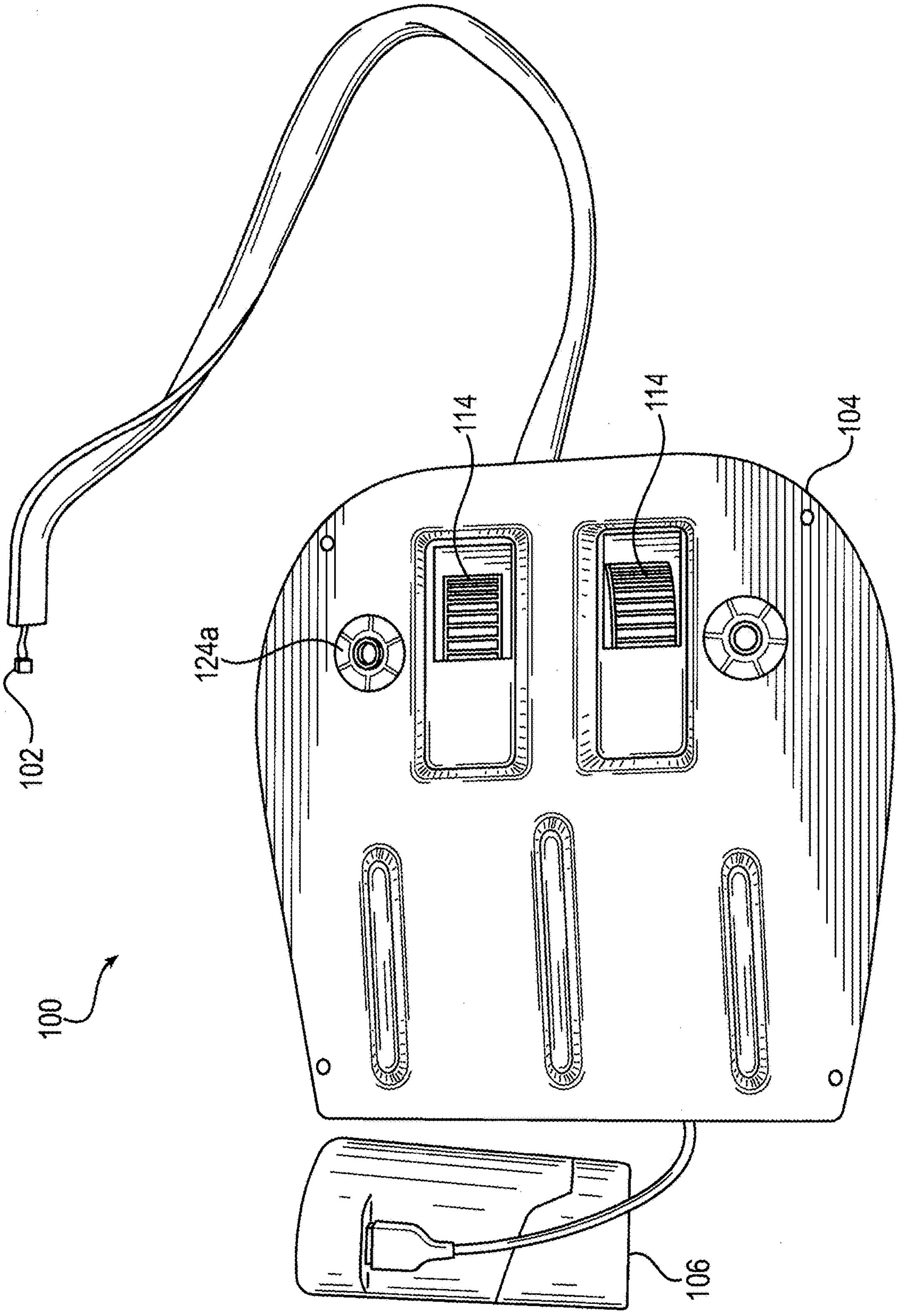
FIG. 4 is a bottom plan view of a ventilation unit and controller device
Figure 5:
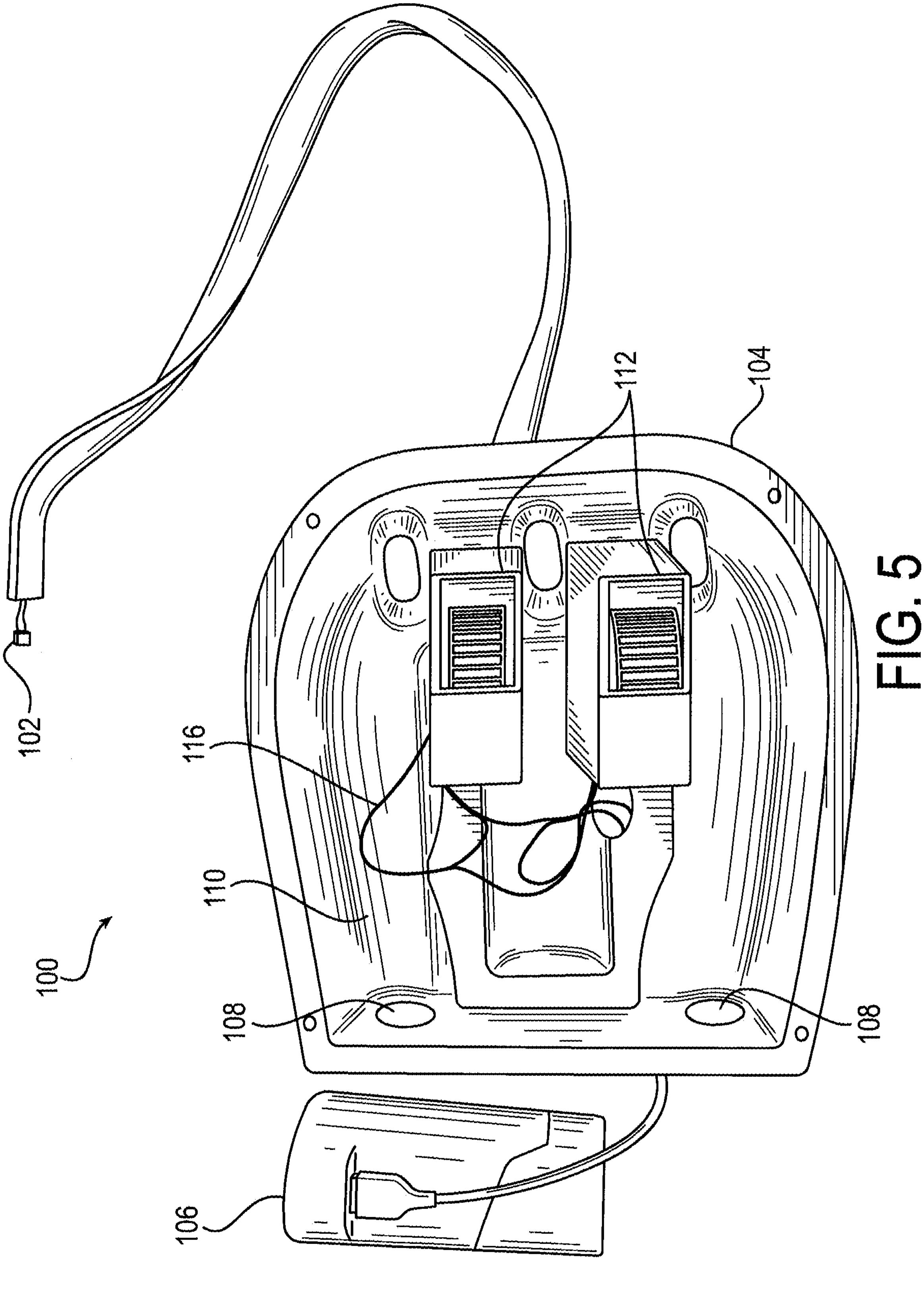
FIG. 5 is a view of a ventilation unit and controller device with a portion of the housing removed

FIGS. 1-5 show an embodiment of a ventilation unit and controller device 100, including a combined sensor and controller 102, housing 104, and source of electric current 106. Intake ports 108, visible in FIG. 1, allow gas, such as air, to flow into a housing cavity 110, which is visible in FIG. 5, and whose dimensions are defined by the contours of the housing 104. Motorized fans 112 positioned inside the housing cavity 110 propel and direct gas into the housing cavity 110 via intake ports 108 and out of the housing cavity 110 via exhaust ports 114, which are shown in FIG. 4. The source of electric current 106 may be a battery, as in the embodiment shown, or may be another suitable source of electric current 106. The source of electric current 106 is conductively connected to the motorized fans 112 by electrical wiring 116.

The combined sensor and controller 102 may be a thermal fuse-type combined sensor and controller 102 positioned such that it will detect an arc flash event in proximity to the sensor and controller 102. The thermal fuse-type combined sensor and controller 102, the source of electric current 106 to the motorized fan 112, and the motorized fan 112 are conductively connected to each other such that thermal fuse-type combined sensor and controller 102 being tripped by the heat resulting from an arc flash event will interrupt power to the motorized fan 112, in turn causing the motorized fan 112 to stop operating or slow down. The combined sensor and controller 102 is conductively connected to other components of the ventilation unit and controller device by, for example, a stereo jack 118. Stereo jack 118 has, for example, a male stereo jack component 118*a*, which reversibly plugs together with a female stereo jack component 118*b* which is conductively connected to the remaining electrical components of the embodiment. Other types of connectors and connections are within the skill of those in the art. In the embodiment shown, the male stereo jack component 118*a* is connected via a wire 116 to the combined sensor and controller 102 so that the male stereo jack component 118*a*, wire 116 and combined sensor and controller 102 may be separated from the rest of the ventilation unit and controller device 100 when the male stereo jack component 118*a* is unplugged from the female stereo jack component 118*b*. An electrical circuit is formed from the interconnected electrical components (i.e., the combined sensor and controller 102, the source of electric current 106, the motorized fans 112, the wire 116, and the stereo jack 118).

It is understood that electrical connections between components of an embodiment of the present invention, such as between components that are conductively connected to each other, may be made in series or in parallel in order to achieve the desired functionality.

Figure 6:
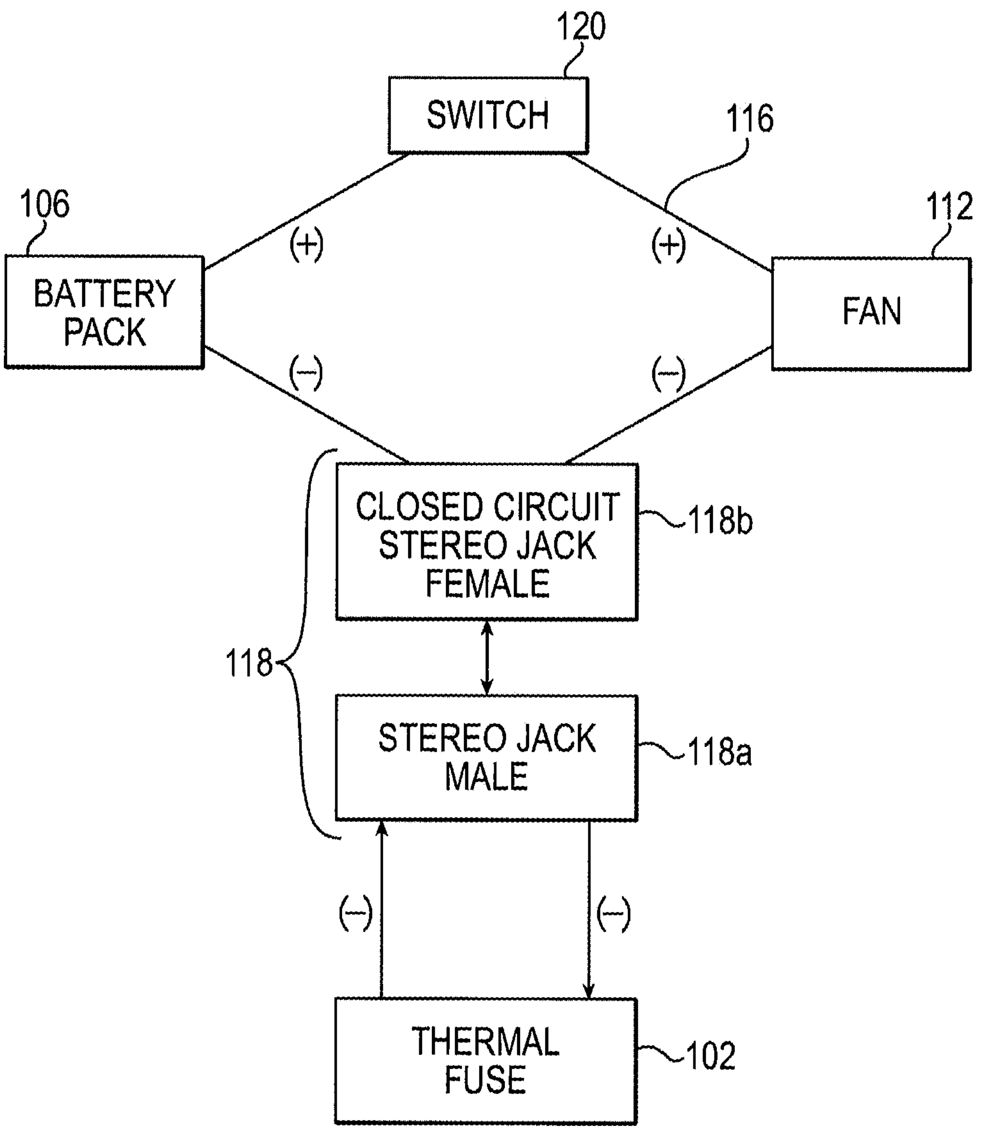
FIG. 6 is a diagram of possible interconnections for components of a ventilation unit and controller device.

In one embodiment, components of the ventilation unit and controller device 100 are interconnected as illustrated in the diagram in FIG. 6. That is, the source of electric current 106, and motorized fan 112 are conductively connected to each other via electrical wiring 116 and a stereo jack 118. A switch 120 (which may be a toggle switch, pushbutton switch, or other type of electrical switch) is conductively connected to the components of the ventilation unit and controller device (e.g., between the source of electric current 106 and the motorized fan 112, so that it is possible to interrupt power to the motorized fan 112 by operating the switch 120, in turn causing the motorized fan 112 to stop operating or slow down. It is to be understood that other arrangements and other combinations of functional components are all within the scope of the embodiments disclosed herein.

Figure 7A:
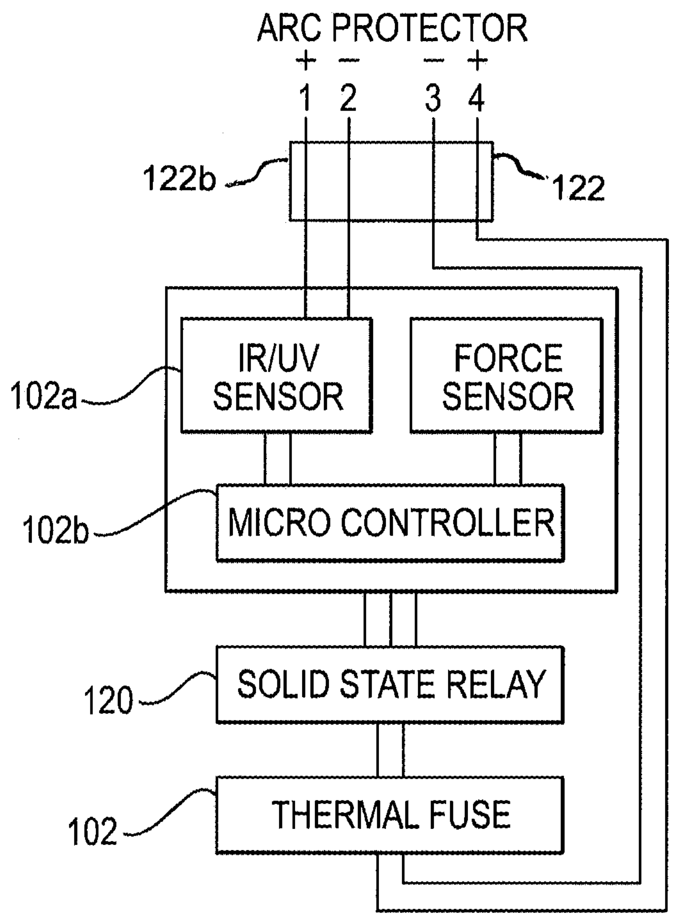
FIG. 7*a* is a diagram of alternative possible interconnections for components of a ventilation unit and controller device.
Figure 7B:
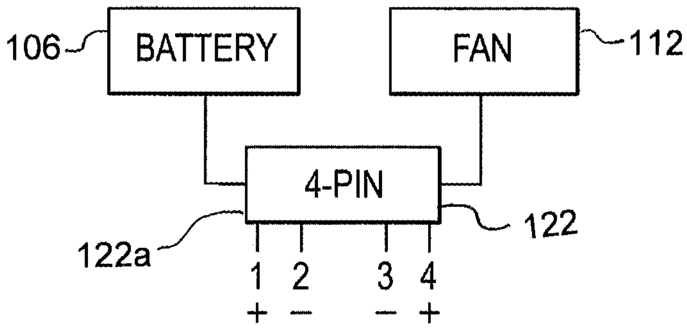
FIG. 7*b* is a diagram of possible interconnections between battery, connector, and fan components of a ventilation unit and controller device.
Figure 7C:
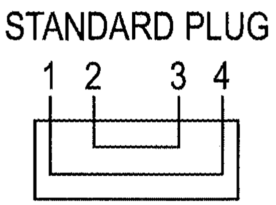
FIG. 7*c* is a diagram of a 4-pin connector plug.

In another embodiment, as shown in the diagrams in FIGS. 7A-7C, a sensor 102*a* and controller 102*b* are physically separate components of the ventilation unit and controller device 100. At least one combined sensor and controller 102 is included in this embodiment as well. The controller 102*b* monitors the condition of one or more sensors 102*a*, or the controller 102*b* may receive signals from one or more sensors 102*a*. The controller 102*b* controls the operation of the motorized fan 112 according to the condition of or signals received from the one or more sensors 102*a*. The combined sensor and controller 102 also controls the operation of the motorized fan 112. The sensor 102*a*, controller 102*b*, and combined sensor and controller 102 are conductively connected to each other via electrical wiring 116. The sensor 102*a* and the combined sensor and controller 102 are capable of sensing an environmental stimulus associated with an arc flash, such as a sudden increase in ambient temperature. The sensing of such environmental stimulus by the sensor 102*a* will result in a signal being sent to the controller 102*b*. The sensing of such environmental stimulus by the combined sensor and controller 102 will result in a reaction by the combined sensor and controller 102.

The embodiment is configured such that components, including the controller 102*b*, sensors 102*a*, and combined sensor and controller 102, connect to each other and to the motorized fan 112 and source of electric current 106 via electrical wiring 116. The electrical wiring 116 between the motorized fan 112 and the source of electric current 106 leads to a connector 122. The connector 122 is a 4-pin connector 122, but in other embodiments it may be some other type of connector 122. The controller 102*b* and sensors 102*a* (or combined sensor and controller 102) is configured with a connector 122 including a male connector component 122*a* and a female connector component 122*b*, such that it can be connected by the connector 122 to other electrical wiring 116 (e.g., electrical wiring 116 connected to the motorized fan 112 and source of electric current 106), so that the motorized fan 112 and source of electric current 106 are capable of being controlled by the controller 102*b* and sensors 102*a* and/or combined sensor and controller 102.

The sensor 102*a* or combined sensor and controller 102 used in the present invention may be of a type capable of sensing one or more environmental factors, stimuli, or changes, including, but not limited to: radiation, acceleration, pressure, force, tilting, light sensor, infrared light, visible light, ultraviolet light, light spectra, temperature, oxygen levels, electromagnetism, magnetism, fumes, organic fumes, inorganic fumes, metal vapors, gases or vapors that follow an arc flash event, images, particulate density, humidity, ozone, carbon monoxide, sound, shrapnel, electrical current, condition evidencing an arc flash event.

It will be understood that more than one sensor 102*a* or combined sensor and controller 102 can be connected in series such that triggering any one of them would result in the interruption of power to the motorized fan 112. Also, more than one sensor 102*a* (or combined sensor and controller 102) can be connected in parallel such that triggering more than one of them is required to result in the interruption of power to the motorized fan 112. It will also be understood that other connecting configurations are possible to change the combinations of sensor 102*a* (or combined sensor and controller 102) tripping that will result in the interruption of power to the motorized fan 112, including having some in series, others in parallel, and combinations of series and parallel configurations. It will also be understood that the invention can be configured such that tripping of the sensor 102*a* (or combined sensor and controller 102) or combination thereof will ultimately affect a control signal to the motorized fan 112 or controller 102*b* (or combined sensor and controller 102) such that tripping of the sensor 102*a* (or combined sensor and controller 102) will control motorized fan 112 operation, even though power to the motorized fan 112 or controller 102*b* (or combined sensor and controller 102) may not be severed.

It will also be understood that the sensors 102*a* (or combined sensor and controller 102) could be wired to directly or indirectly control power to a diverter, sphincter, valve, or other or other mechanical device capable of restricting the movement of gas through the ventilation unit and controller device 100. It will also be understood that the invention can be configured such that tripping of the sensor 102*a* (or combined sensor and controller 102) or combination of sensors 102*a* (or combination of combined sensor and controller 102) will affect a control signal to the diverter, sphincter, valve, or other or other mechanical device capable of restricting the input of ambient air, such that tripping of the sensor or sensors will restrict the movement of gas through the ventilation unit and controller device 100, even though power may not be severed.

The controller 102*b* (or combined sensor and controller 102) may comprise a microcontroller, Field Programmable Gate Array (FPGA), or Application-Specific Integrated Circuit (ASIC), -type controller 102*b* (or combined sensor and controller 102) or other electronic circuitry.

Also, the controller 102*b* (or combined sensor and controller 102) may comprise a solid state relay, a relay, a solenoid, a thyristor, a Field-Effect Transistor (FET)-type controller 102*b* (or combined sensor and controller 102), or other electronic circuitry that controls or interrupts a signal passing through the controller 102*b* (or combined sensor and controller 102), or controls an output signal from the controller. The controller 102*b* (or combined sensor and controller 102) may alternatively be configured to interact with a solid state relay, a relay, a solenoid, a thyristor, a FET, or other electronic circuitry or switch 120 that is included in a ventilation unit.

Figure 10:
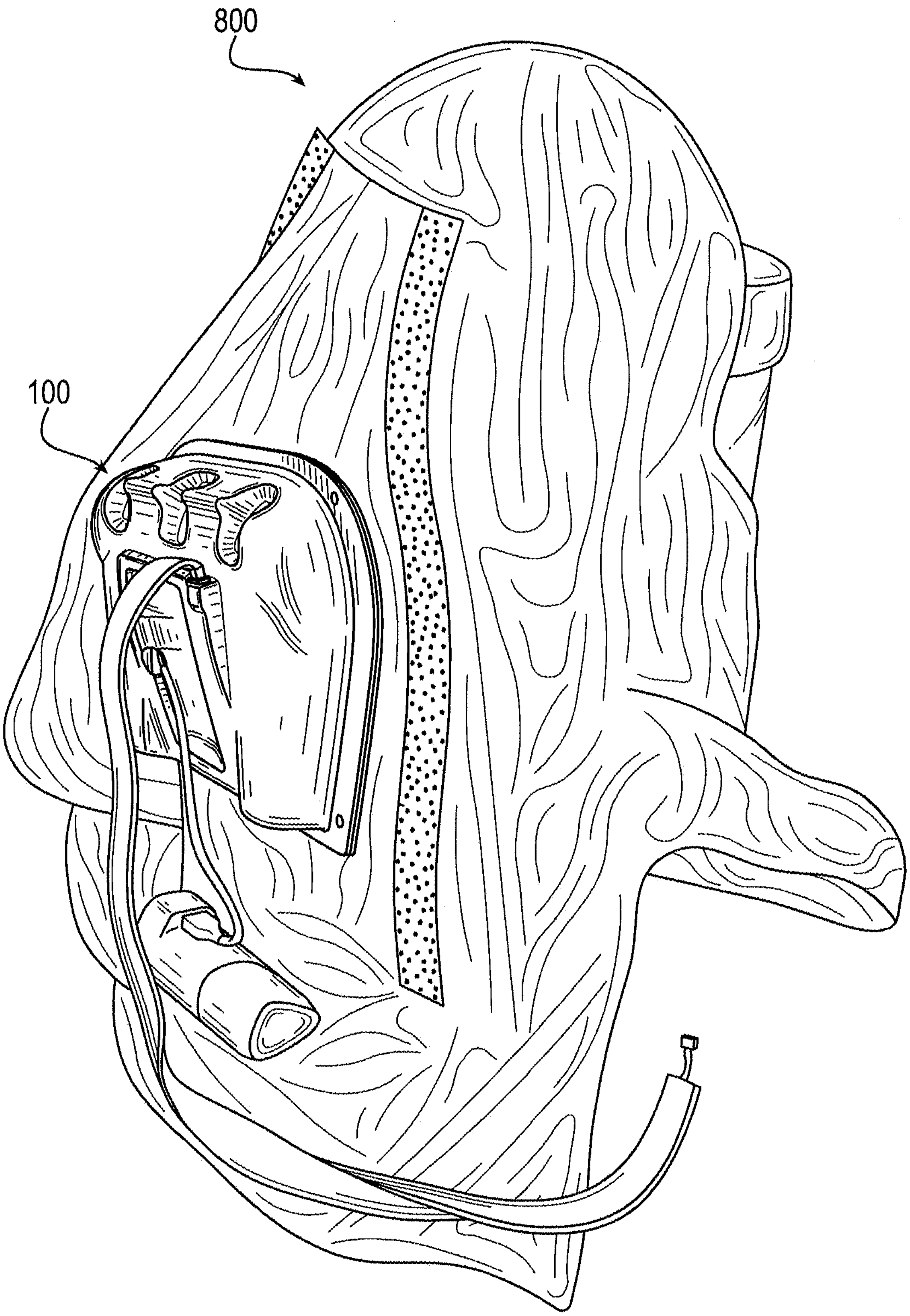
FIG. 10 is a right side perspective view of an arc flash hood with a cutaway view of a rear flap exposing a ventilation unit and controller device connected to the arc flash hood at the ventilation unit and controller device connection port of the arc flash hood.
Figure 11:
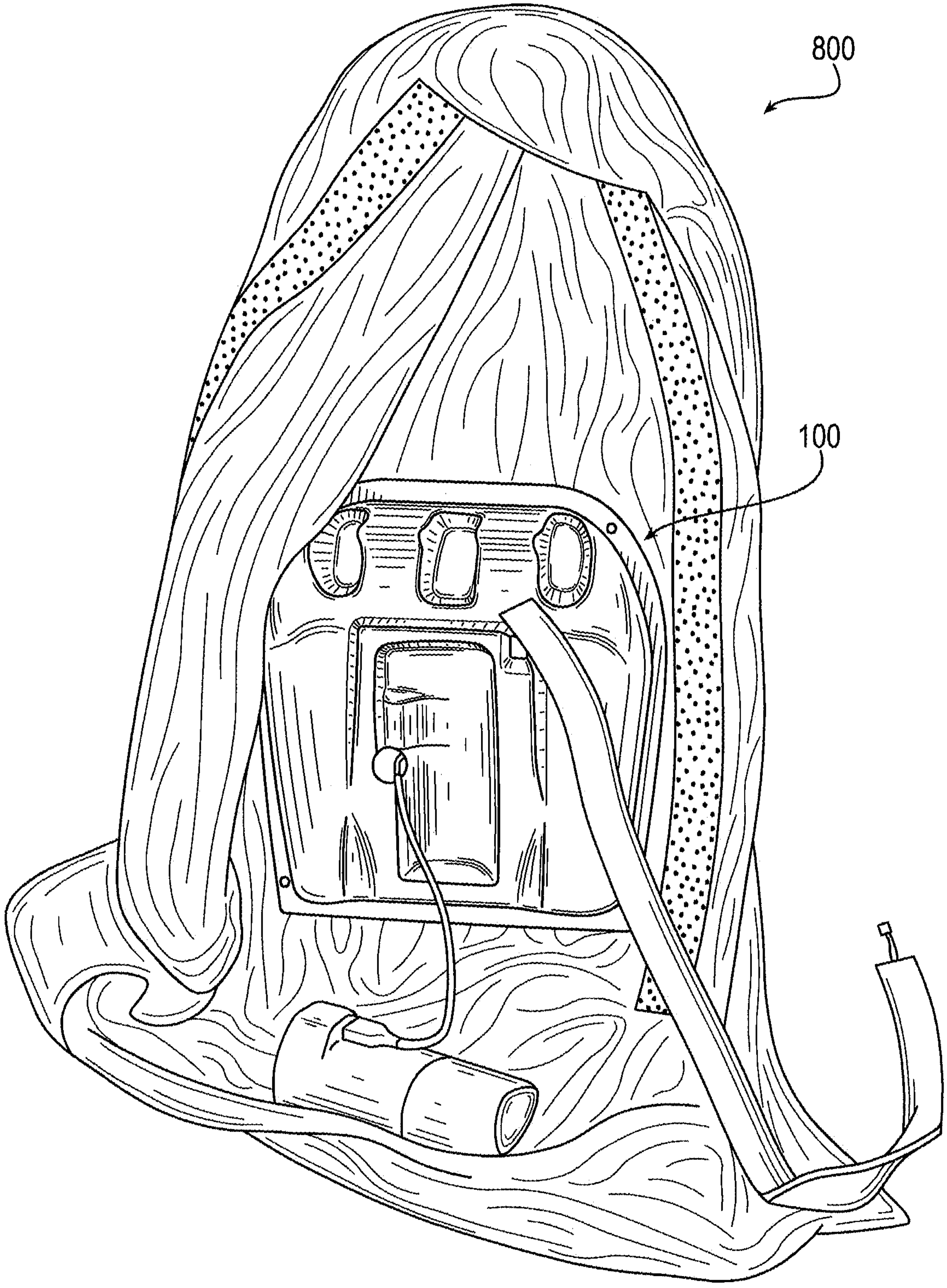
FIG. 11 is a rear perspective view of an arc flash hood with a cutaway view of a rear flap exposing a ventilation unit and controller device connected to the arc flash hood at the ventilation unit and controller device connection port of the arc flash hood.

The ventilation unit and controller device 100 may be mounted on or connected to an arc flash hood 800 (shown in FIGS. 8-11). The arc flash hood 800 has a ventilation opening 802 to permit gas (not shown) exiting from the exhaust port 114 of the ventilation unit and controller device 100 to enter the arc flash hood 800. Complementary male fastener components 124*a* and female fastener components 124*b* mounted on the arc flash hood 800 and the ventilation unit and controller device 100 allow for the coupling of the ventilation unit and controller device 100 with the arc flash hood 800, as shown in FIGS. 10-11.

In other embodiments (not shown), the ventilation unit and controller device 100 is mounted on a mask, resembling a scuba mask or a fireman's mask, or other breathing device.

In other embodiments (not shown), the motorized fan 112 may be mounted on or connected to an arc flash hood 800 directly, or it may be connected to the arc flash hood 800 via tubes or hoses or other means for carrying gas such as air (not shown). As stated above, the sensor 102*a* and the controller 102*b* may be combined into one combined sensor and controller 102 unit. The sensor 102*a* may be a separate unit that is physically separate from the controller 102*b*, arc flash hood 800, or arc flash suit and communicates with the controller via electrical connectors, electrical wiring 116, fiber optics, free-space optics, wireless communication such as Wi-Fi, Bluetooth, or the like, or other means of communication. There may be more than one sensor 102*a*, and the controller 102*b* may react according to feedback from one or more of the sensors 102*a*. The sensor 102*a* may be located outside of or inside the arc flash hood 800. The sensor 102*a* may be placed at various locations inside the arc flash hood, such as, for example, near the cheek of the user in location 130 in FIG. 8*a*

Figure 8:
FIG. 8 is front perspective view of an arc flash hood.
Figure 8A:
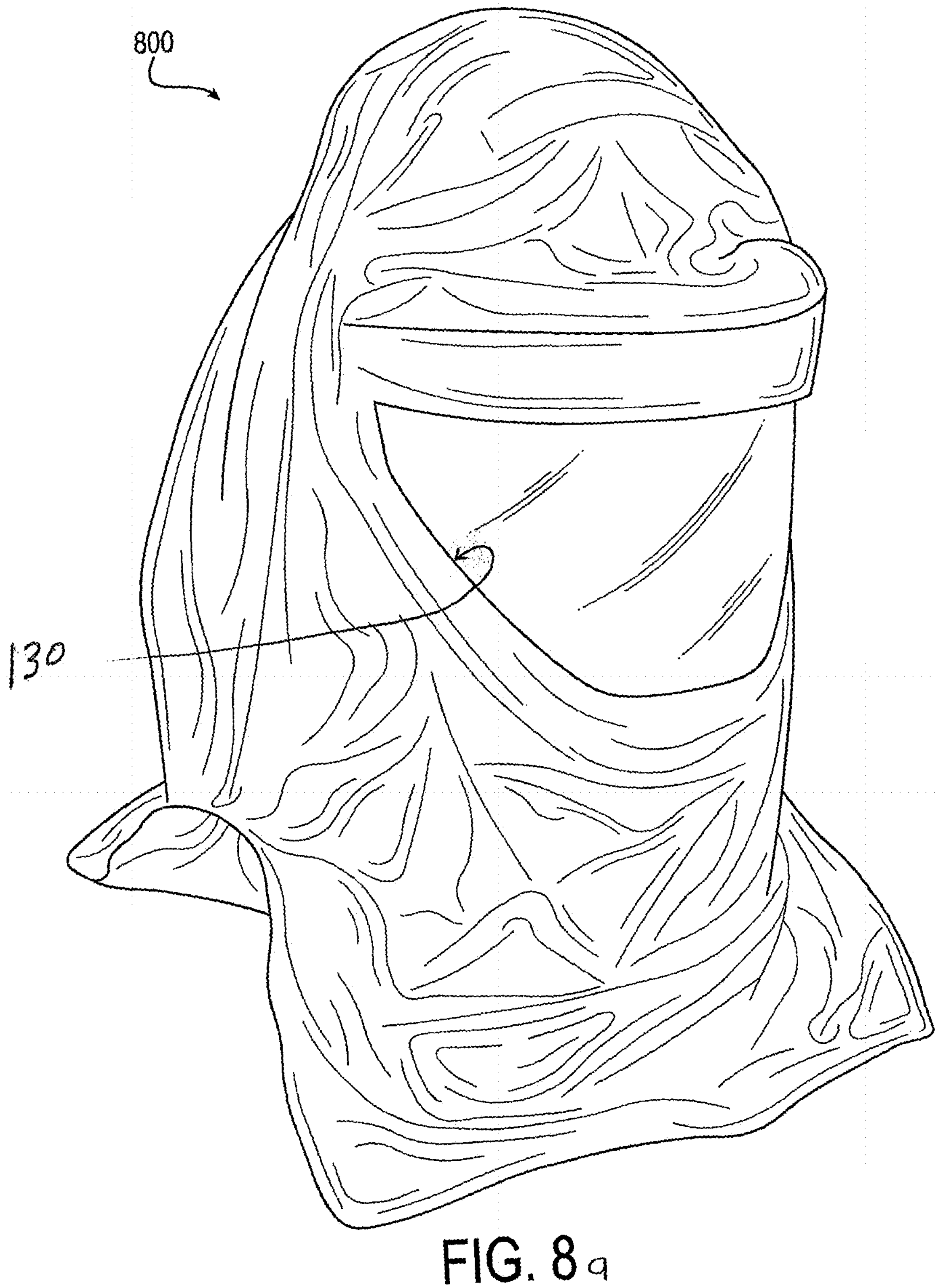
FIG. 8*a* is a front perspective view of another embodiment of the arc flash hood.
Figure 9:
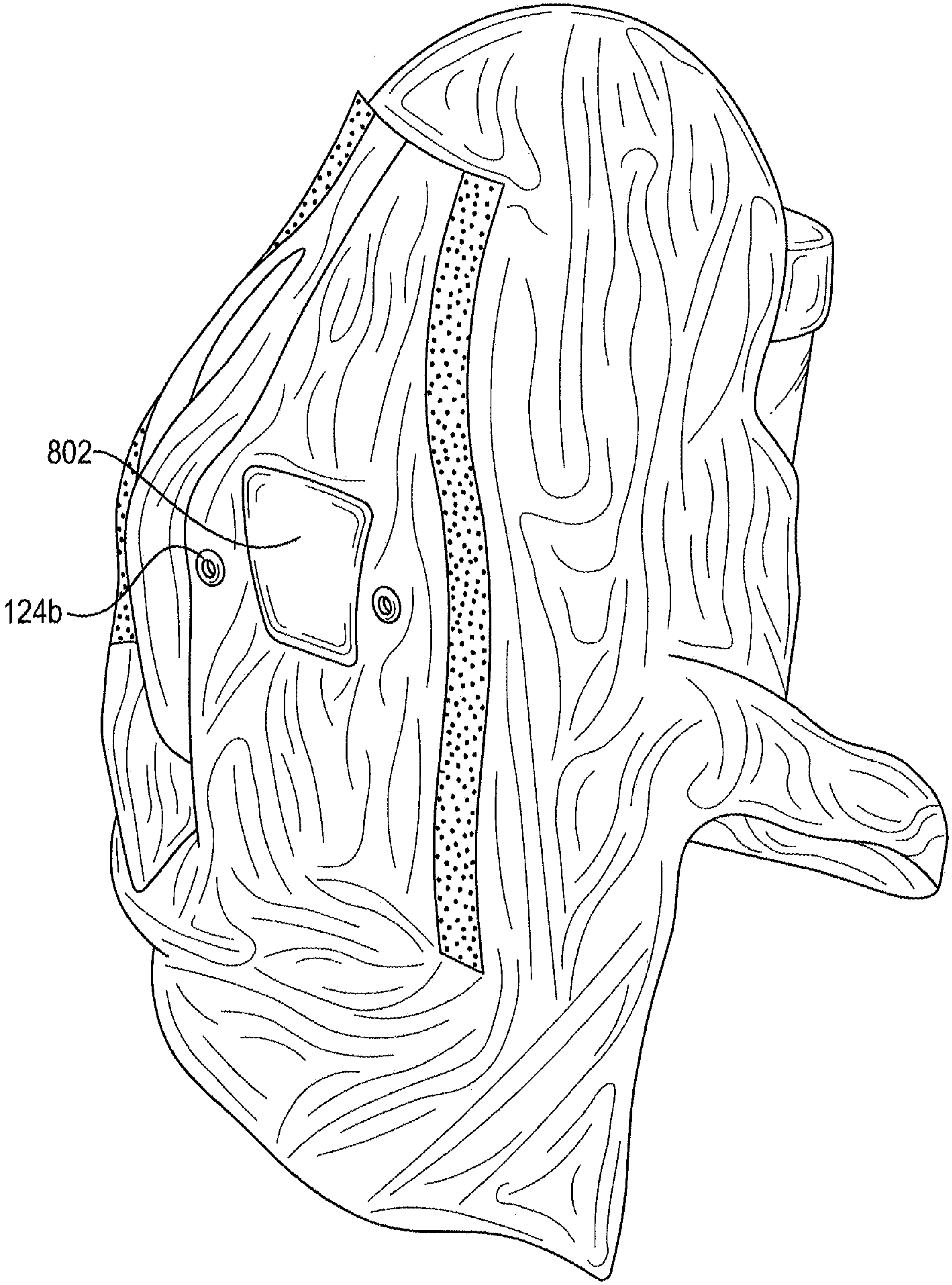
FIG. 9 is a right side perspective view of an arc flash hood with a cutaway view of a rear flap exposing a ventilation unit and controller device connection port and means of attachment.

In another embodiment the sensor 102*a* is located inside the arc flash hood 800 at location 130, as shown in FIG. 8*a*, and it includes an oxygen sensor, a temperature sensor or both constructed to send signals to the controller 102*b*. The controller 102*b* and sensor 102*a* are configured to control the oxygen level and the temperature inside the arc flash hood 800, and to operate the variable speed motorized fan 112 to change the temperature and/or oxygen levels inside the arc flash hood 800. For example, in one embodiment, if the temperature is at a comfortable level but the oxygen level is low, the variable speed motorized fan 112 will turn on low speed to restore oxygen levels but not cool the user. Alternatively, if the oxygen level is acceptable, but the temperature is too high, the variable speed motorized fan 112 will turn on high speed to cool the user. Other responses to the oxygen level and temperature are within the scope of the invention.

From the description above, advantages of the embodiments of the invention become evident in that they allow for a ventilation unit and controller device 100 for use with an arc flash hood or protective suit that is capable of stopping, increasing or slowing the input of outside air following in response to environmental conditions.

While the invention has been described by reference to various specific embodiments, it should be understood that numerous changes may be made within the spirit and scope of the inventive concepts described. Accordingly, it is intended that the invention not be limited to the described embodiments, but will have full scope defined by the language of the following claims.

What is claimed is:

1. An arc flash hood comprising:

a) a ventilation unit attached to the arc flash hood and in fluid communication therewith including a housing with an intake port permitting flow of gas into the housing and an exhaust port permitting flow of gas out of the housing;

b) a variable speed motorized fan positioned within the housing to direct gas into the housing via said intake port and out of the housing via the exhaust port;

c) a controller capable of controlling the ventilation unit;

d) a source of electric current to a circuit to power the ventilation unit; and e) an oxygen sensor and a temperature sensor mounted within the arc flash hood wherein the controller varies the speed of the variable speed motorized fan in response to signals from the oxygen sensor and the temperature sensor to regulate the oxygen level and the temperature within the arc flash hood, wherein the controller is configured to receive signals from both the oxygen sensor and the temperature sensor and to vary the speed of the variable speed motorized fan according to a multi-parameter logic that prioritizes restoration of oxygen level when the oxygen level is below a threshold and the temperature is within a comfortable range, and prioritizes cooling when the temperature is above a threshold and the oxygen level is within an acceptable range.

2. The arc flash hood of claim 1, wherein the ventilation unit and said controller are combined to form a combined ventilation unit and controller.

3. The arc flash hood of claim 1, further comprising a mechanical device capable of restricting the movement of gas and capable of being controlled by the controller.

4. The arc flash hood of claim 1, wherein the ventilation unit is removably attached to the arc flash hood.

* * * * *